US011944822B2

(12) United States Patent
Hess et al.

(10) Patent No.: US 11,944,822 B2
(45) Date of Patent: Apr. 2, 2024

(54) HIGH DENSITY NEURAL IMPLANT CYLINDRICAL PACKAGING

(71) Applicant: Neuralink Corp., Fremont, CA (US)

(72) Inventors: Joshua S. Hess, Dublin, CA (US); Mark J. Smith, Fremont, CA (US)

(73) Assignee: NEURALINK CORP., Fremont, CA (US)

( * ) Notice: Subject to any disclaimer, the term of this patent is extended or adjusted under 35 U.S.C. 154(b) by 400 days.

(21) Appl. No.: 17/464,553

(22) Filed: Sep. 1, 2021

(65) Prior Publication Data

US 2023/0063165 A1 Mar. 2, 2023

(51) Int. Cl.
*H05K 9/00* (2006.01)
*A61N 1/372* (2006.01)
*H05K 1/14* (2006.01)
*H05K 3/36* (2006.01)

(52) U.S. Cl.
CPC ......... *A61N 1/37229* (2013.01); *H05K 1/141* (2013.01); *H05K 3/361* (2013.01); *H05K 9/0067* (2013.01)

(58) Field of Classification Search
CPC ....... H05K 1/141; H05K 3/361; H05K 9/0067
See application file for complete search history.

(56) References Cited

U.S. PATENT DOCUMENTS

| | | | | |
|---|---|---|---|---|
| 4,997,377 A | * | 3/1991 | Goto | H05K 1/118 439/640 |
| 5,026,291 A | * | 6/1991 | David | H01R 12/79 439/493 |
| 5,161,986 A | * | 11/1992 | Gulbranson | H01R 12/714 439/493 |
| 2016/0249820 A1 | * | 9/2016 | Puig | A61B 5/681 600/479 |
| 2016/0252313 A1 | * | 9/2016 | Zieglturm | F28D 5/02 165/301 |
| 2016/0294090 A1 | * | 10/2016 | Yang | H05K 3/3405 |
| 2017/0111993 A1 | * | 4/2017 | Lang | F21V 23/06 |
| 2021/0051801 A1 | * | 2/2021 | Chuah | H05K 1/181 |

OTHER PUBLICATIONS

"Airpods Pro Teardown," Teardown, Oct. 31, 2019, 15 pages.
"Teardown: Jabra Elite 65t," GlobalSpec, Electronics 360, Aug. 9, 2019, 6 pages.
Knowles, "Samsung Gear IconX Teardown," Radtenna Ltd., Oct. 25, 2016, 12 pages.
Savov, "Powerbeats Pro Teardown Shows Commonalities with Airpods and Galaxy Buds," The Verge, Jun. 9, 2019, 2 pages.

* cited by examiner

*Primary Examiner* — Phuong Chi Thi Nguyen
(74) *Attorney, Agent, or Firm* — Kilpatrick Townsend & Stockton LLP

(57) ABSTRACT

A space-saving configuration for electronics is disclosed in which at least four circuit boards are arranged to form sides of a five-or-greater sided geometric prism that are perpendicular to a common plane. That is, they are stood up on their sides and connected with flex cable to approximate a cylinder. Each circuit board can include one or more sides with electrical components. The circuit boards make up at least half of the five-or-greater sided geometric prism such that the circuit boards wrap at least halfway around. A common connector on one of the circuit boards can be configured to receive power from an underlying motherboard, and flex cables connecting adjacent circuit boards in series distribute power received from the connector to each of the circuit boards in series.

20 Claims, 11 Drawing Sheets

HIGH DENSITY NEURAL IMPLANT CYLINDRICAL PACKAGING

CROSS-REFERENCES TO RELATED APPLICATIONS

Not Applicable

STATEMENT AS TO RIGHTS TO INVENTIONS MADE UNDER FEDERALLY SPONSORED RESEARCH AND DEVELOPMENT

Not Applicable

BACKGROUND

1. Field of the Invention

Embodiments of the present disclosure generally relate to electronics assemblies. More specifically, embodiments relate to apparatuses and processes for high density neural implant assemblies.

1. Description of the Related Art

Implantable devices can be implanted into neurological tissue, such as the brain, to form a brain-computer interface. In certain instances, the implantable devices can contain a biocompatible substrate with conduits for stimulation of neurons and/or recording neuronal signals.

Such neuronal signals may be faint, analog, unprocessed signals, and may be preprocessed through analog-to-digital conversion, aggregation, and conversion to data packets and/or to human- or machine-readable formats, before being analyzed or otherwise processed by a computer within the implant and/or transmitted to another computer outside of the implant. The electrical components performing the pre-processing, transmission, and/or analysis, and the power sources enabling such processing, add to the overall volume of an implantable device.

However, space is often a primary constraint in neural implants, as larger implants may lead to tissue damage. Accordingly, increasing the density and compactness of electronics packaging while maintaining a high level of performance may improve the overall viability of neural implants as brain-computer interfaces.

BRIEF SUMMARY

Generally, multiple circuit boards can be wrapped in a cylindrical fashion to form sides of a geometric prism. Flex cables connecting adjacent circuit boards in series around the perimeter of the geometric prism provide data and power transmission between the circuit boards. Additional components, such as inductive charging coils and antennas, can then be arranged around the circumference of the cylindrically wrapped circuit boards. Other components, such as a battery, can be placed in the center of the cylindrically wrapped circuit boards. Arranging the multiple circuit boards and other components of an electronic device in the form of concentric cylinders reduces the overall height of the device compared to stacking components in parallel planes.

Further, inductive charging coils, or power coils, may be designed to reduce the overall height of electronic devices by wrapping the power coil around the perimeter of the device and/or other electronic components, such as circuit boards, as opposed to being stacked above or below the components. The power coil can be made from a planar, or ribbon like, conducting material with a rectangular cross section. The conducting material may then be wrapped in a spiral fashion around the length of the conducting material to form a geometric cylinder with an opening in the middle. One or more electrical components, such as one or more circuit boards, may then be placed within the opening of the cylinder. The additional field lines captured by the planar conducting material may provide increased power transfer efficiency and less loss at a lower total volume due to a higher surface area to volume ratio.

The present disclosure is related to a space-saving, wrapped cylindrical electronic apparatus including a plurality of at least four circuit boards arranged to form sides of a five-or-greater sided geometric prism that are perpendicular to a common plane, wherein each circuit board of the plurality of circuit boards includes a side with electrical components. The plurality of circuit boards comprises at least half of the five-or-greater sided geometric prism such that the circuit boards wrap at least halfway around said geometric prism. The apparatus may further include a connector on one of the circuit boards configured to receive power, and flex cables connecting adjacent circuit boards in series. The flex cables may distribute power received from the connector to each of the circuit boards in series.

In a further embodiment, the wrapped cylindrical electronic apparatus further includes a power coil disposed around the geometric prism and electrically coupled to the plurality of circuit boards. The power coil comprises a planar conducting material having a length, wherein the length of the planar conducting material is wrapped in a spiral thereby forming a geometric cylinder.

In a further embodiment, the wrapped cylindrical electronic apparatus further includes a ferrimagnetic cup having a cylindrical side wall, wherein the plurality of circuit boards are arranged within an interior of the ferrimagnetic cup such that the side with electrical components of each circuit board of the plurality of circuit boards faces the cylindrical side wall.

In some embodiments, the ferrimagnetic cup is configured to align the plurality of circuit boards in a predefined orientation within the ferrimagnetic cup.

In a further embodiment, the wrapped cylindrical electronic apparatus further includes a cylindrical button battery around which the circuit boards are arranged.

In a further embodiment, the wrapped cylindrical electronic apparatus further includes a radio antenna electrically coupled to at least one of the plurality of circuit boards. The radio antenna may form a circular loop with a circumference in a first plane parallel to the common plane.

In a further embodiment, the wrapped cylindrical electronic apparatus further includes a chassis, wherein each circuit board of the plurality of circuit boards is mechanically secured to the chassis.

In a further embodiment, the wrapped cylindrical electronic apparatus further includes a circular circuit board electrically coupled to the plurality of circuit boards disposed parallel to the common plane.

In a further embodiment, the wrapped cylindrical electronic apparatus further includes a metallic shield connected to the circular circuit board, wherein the metallic shield is continuously connected around a circumference of the circular circuit board.

Some embodiments of the present disclosure are related to a three dimensional wrapped cylindrical electronic apparatus including a power coil comprising a planar conducting material having a length, wherein the length of the planar conducting material is wrapped in a spiral thereby forming a geometric cylinder. The three dimensional wrapped cylindrical electronic apparatus may further include a circuit board, including a side with electrical components, electrically coupled to the power coil and disposed within an interior of the geometric cylinder such that the side of the circuit board faces the planar conducting material. The three dimensional wrapped cylindrical electronic apparatus may further include a ferrimagnetic cup having a planar base and a cylindrical side wall, wherein the ferrimagnetic cup is disposed within the geometric cylinder such that the cylindrical side wall separates the power coil from the circuit board.

In a further embodiment, the three dimensional wrapped cylindrical electronic apparatus may further include a radio antenna electrically coupled to the circuit board. The radio antenna can form a circular loop and be arranged on an exterior surface of the ferrimagnetic cup such that the circular loop is parallel to the planar base of the ferrimagnetic cup.

In a further embodiment, the three dimensional wrapped cylindrical electronic apparatus may further include a chassis arranged within the ferrimagnetic cup, wherein the circuit board is secured to the chassis.

In a further embodiment, the three dimensional wrapped cylindrical electronic apparatus may further include a circular circuit board electrically coupled to the circuit board disposed parallel to the planar base of the ferrimagnetic cup and perpendicular to the side of the circuit board.

Some embodiments of the present disclosure are related to a method of manufacturing a space-saving, wrapped cylindrical electronic apparatus, the method including: providing a plurality of at least four circuit boards, each circuit board of the plurality of circuit boards including a side with electrical components, wherein at least one circuit board of the plurality of circuit boards includes a connector configured to receive power; arranging the plurality of circuit boards to form sides of a five-or-greater sided geometric prism that are perpendicular to a common plane, wherein the plurality of circuit boards comprises at least half of the five-or-greater sided geometric prism such that the plurality of circuit boards wraps at least halfway around said geometric prism; and connecting adjacent circuit boards in series using flex cables, the flex cables distributing power received from the connector to each circuit board of the plurality of circuit boards in series.

The method can further include: electrically coupling a power coil to the plurality of circuit boards, the power coil comprising a planar conducting material having a length; and wrapping the length of the planar conducting material around the geometric prism thereby forming a geometric cylinder.

The method can further include: providing a ferrimagnetic cup having a cylindrical side wall; and arranging the plurality of circuit boards within an interior of the ferrimagnetic cup such that the side with electrical components of each circuit board of the plurality of circuit boards faces the cylindrical side wall.

The method can further include: electrically coupling a radio antenna to at least one of the plurality of circuit boards, the radio antenna forming a circular loop with a circumference in a first plane; and arranging the circular loop adjacent to the plurality of circuit boards such that the first plane is parallel to the common plane.

The method can further include electrically coupling a circular circuit board to the plurality of circuit boards; and disposing the circular circuit board parallel to the common plane.

The method can further include connecting a metallic shield to the circular circuit board, wherein the metallic shield is continuously connected around a circumference of the circular circuit board.

The method can further include mechanically securing each circuit board of the plurality of circuit boards to a chassis

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Advancements in electronics, from increased processing power to decreased form factors, have enabled new possibilities and applications previously unthinkable in the past.

However, while these advancements continue to take place, there are constant pressures in many fields to further reduce the overall volume of electronic devices and/or produce electronic devices within constrained shapes while maintaining a high level of performance.

This is especially true in the field of neural implants. While electronic components may be stacked one on top of the other in electronic devices for many fields and applications, this may not be the case for neural implants as taller devices may contribute to tissue erosion within a patient.

In addition to the size and form constraints, neural implants provide a unique challenge due to their relative inaccessibility once implanted in a human. As with many electrical devices, neural implants require electricity from a power source, such as a battery. However, while other devices may provide ready access to the battery or a connection to charge the battery, the power source for neural implants is often charged wirelessly, such as through an induction coil, in order minimize the risk of infection. Similarly, neural implants may rely on radio transmission to provide the valuable information collected from within the brain to an external device. Finally, high performance, and often highly specialized, computer chips may be used to collecting and process the neuronal signals into data in the first place. Each of these physical components take up space in the real world. However, the arrangement and placement of these components may be selected to increase the overall density of the implant and thereby reduce space and/or volume.

Embodiments of the present disclosure address these challenges using novel approaches to packaging and/or assembling electronic components within electronic devices, such as neural implants. Wrapping electrical components and systems in a cylindrical fashion, as opposed to flat stacking each component, allows for nesting of multiple components within concentric cylinders of electrical components. Cylindrically wrapped devices may reduce the overall height of the device and increase the density. This may also allow, in several instances, for the combination and/or reduction of components, thereby increasing the simplicity and robustness of a device.

Further detail regarding high density cylindrically wrapped electronic devices is provided in relation to the figures.

Figure 1:
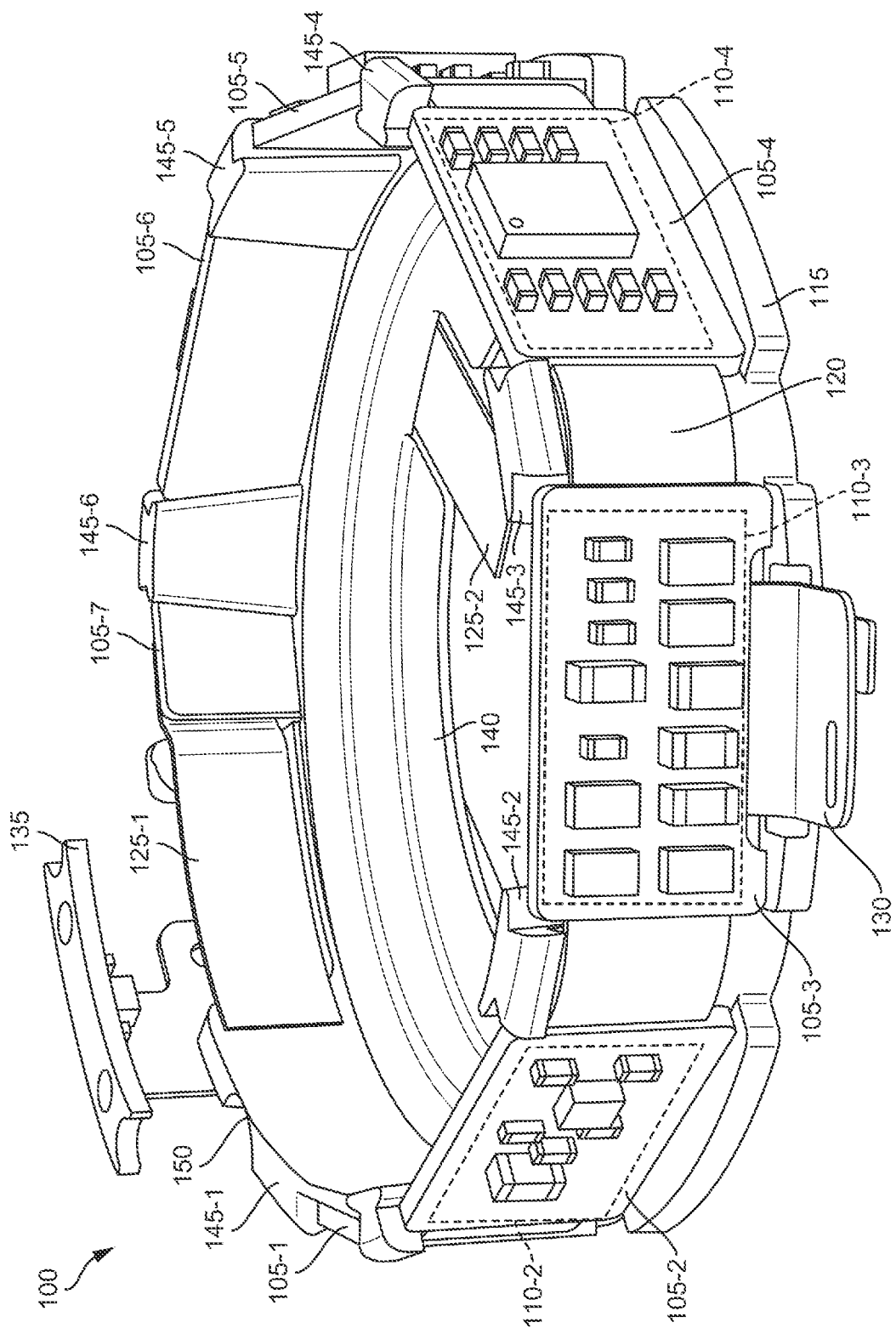
FIG. 1 illustrates a side-top view an assembly of cylindrically wrapped electronics with a chassis, according to embodiments of the present disclosure.

FIG. 1 illustrates a side-top view an assembly 100 of cylindrically wrapped electronics with a chassis, according to embodiments of the present disclosure. Assembly 100 includes a plurality of circuit boards 105 and a chassis 115. The plurality of circuit boards 105 includes at least four circuit boards. For example the plurality of circuit boards 105 includes a first circuit board 105-1, a second circuit board 105-2, a third circuit board 105-3, a fourth circuit board 105-4, a fifth circuit board 105-5, a sixth circuit board 105-6, and a seventh circuit board 105-7. Each circuit board of the plurality of circuit boards 105 is a printed circuit board (PCB) with conductive layers separated by layers of substrate. It may be a flexible PCB, a rigid PCB, or some combination of rigid and flexible PCB.

One or more of the plurality of circuit boards 105 includes at least one side with electrical components. For example, second circuit board 105-2 includes electrical components 110-2, third circuit board 105-3 includes electrical components 110-3, and fourth circuit board 105-4 includes electrical components 110-4. Additionally or alternatively, one or more of the plurality of circuit boards 105 may include electrical components on both sides of the circuit board. Electrical components 110 include any combination of resistors, capacitors, inductors, integrated circuits, transistors, and/or sensors.

The plurality of circuit boards 105 are arranged in a cylindrical fashion. For example, the plurality of circuit boards 105 are arranged to form sides of a seven sided geometric prism. The sides of the geometric prism correspond to the polygon base of the geometric prism, such that the geometric prism has the same number of sides as the polygon base. The polygon base is perpendicular to the sides of the geometric prism and forms a common plane. Each of the plurality of circuit boards 105 are perpendicular to the common plane formed by the polygon base of the geometric prism. As illustrated, the plurality of circuit boards form each side of the geometric prism.

While illustrated as a seven sided geometric prism, the geometric prism may have any number of sides, as described further below. For example, the plurality of circuit boards may be arranged to form sides of a five or greater sided geometric prism. The plurality of circuit boards 105 may comprise any number of sides of the geometric prism up to, and including, each side. For example, the plurality of circuit boards 105 may be form at least half of the sides of the geometric prism, such that the circuit boards wrap at least halfway around the geometric prism, as described below.

One or more circuit boards of the plurality of circuit boards 105 includes one or more connectors configured to receive power. For example, power connectors 125 are coupled with seventh circuit board 105-7 and/or sixth circuit board 105-6 and are configured to receive power from a power source. The power source may be a battery, such as a button cell battery, as described below. In this example, power connector 125-1 may make contact with a cathode casing, or positive terminal, of a button cell battery, while power connector 125-2 may make contact with an anode cap, or negative terminal, of the button cell battery, thereby receiving power from the button cell battery.

Additionally or alternatively, one or more connectors may be configured to receive power from a power coil. For example, third circuit board 105-3 includes power coil connector 130 configured to be connected to a power coil. The power coil may be a wireless charging coil configured to charge a battery, such as a button cell battery, as described below. One or more circuit boards of the plurality of circuit boards 105 may also be electrically coupled to a radio antenna. For example, antenna connector 135 electrically couples one or more circuit boards of the plurality of circuit boards 105 with a radio antenna, as described below.

Adjacent circuit boards of the plurality of circuit boards 105 are connected in series by one or more flex cables. For example, third circuit board 105-3 is connected to fourth circuit board 105-4 by flex cable 120. The one or more flex cables may distribute power received from a power connector, such as power connector 125-1, to each circuit board of the plurality of circuit boards 105 in series. The one or more flex cables may also transmit data between adjacent circuit boards. For example, flex cable 120 may transmit data and/or distribute power from fourth circuit board 105-4 two third circuit board 105-3 and vice versa.

Each circuit board of the plurality of circuit boards 105 are mechanically secured to chassis 115. Chassis 115 can be made from any rigid and/or semi rigid material, such as plastic. Chassis 115 includes circular base 140 and one or more support structures 145 disposed around the outer circumference of circular base 140 and perpendicular to circular base 140. Chassis 115 also includes one or more alignment features configured to align chassis 115 with other components, as described below. For example, chassis 115 includes notch 150 running perpendicular to circular base 140 in support structure 145-1.

Chassis 115 is configured to restrain each component of assembly 100 in a predefined position and/or orientation, such as to form the sides of a geometric prism with the plurality of circuit boards 105. For example, the one or more support structures 145 include connection points for each circuit board of the plurality of circuit boards 105 such that when the plurality of circuit boards 105 are mechanically connected to the connection points, the plurality of circuit boards 105 form sides of the geometric prism. As another example, chassis 115 includes one or more surfaces between the connection points such that when the plurality of circuit boards 105 are mechanically connected to the connection points, the one or more surfaces maintain a predefined bend radii of the one or more flex cables 120 between each circuit board of the plurality of circuit boards 105.

FIGS. 2A-2F illustrate arrangements of circuit boards to form various geometric prisms, according to embodiments of the present disclosure. As described above, a plurality of circuit boards, such as circuit boards 105, are arranged to form sides of a five or greater sided geometric prism. The sides of the geometric prism correspond to sides of the polygon base of the geometric prism, such that the geometric prism has the same number of sides as the polygon base. The figures illustrate a polygon base 205 of a geometric prism as viewed from above or below, with a plurality of circuit boards 105 arranged to form sides of the geometric prism such that the plurality of circuit boards 105 make up at least half of the five or greater sided geometric prism and wrap at least halfway around the geometric prism.

Figure 2A:
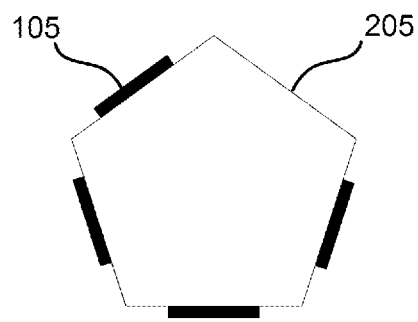
FIGS. 2A-2F illustrate arrangements of circuit boards to form various geometric prisms, according to embodiments of the present disclosure.

FIG. 2A illustrates a geometric prism with a five sided polygon base 205 and four circuit boards 105 arranged to form four sides of the geometric prism.

Figure 2B:
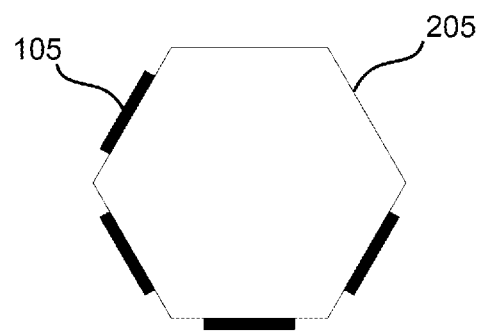

FIG. 2B illustrates another example where four circuit boards 105 are arranged to form four sides of a geometric prism with a six sided polygon base 205. As illustrated in both of the above examples, the four circuit boards 105 comprise at least half of the sides of the geometric prism, and wrap at least halfway around the geometric prism.

Figure 2C:
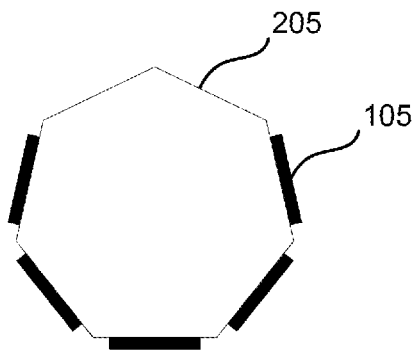

FIG. 2C illustrates a geometric prism with a seven sided polygon base 205 and five circuit boards 105 arranged to form five sides of the geometric prism.

Figure 2D:
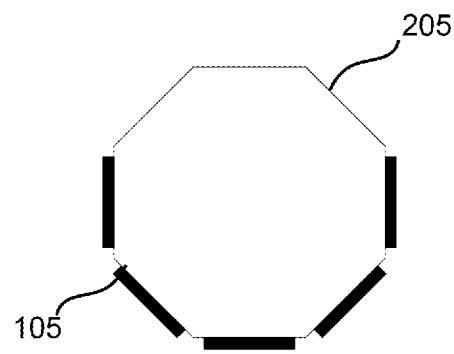

FIG. 2D illustrates another example where five circuit boards 105 are arranged to form five sides of a geometric prism with an eight sided polygon base 205. As illustrated in both examples, the five circuit boards 105 comprise at least half of the sides of the geometric prism, and wrap at least halfway around the geometric prism.

Figure 2E:
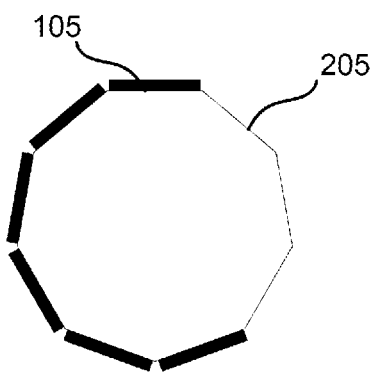

FIG. 2E illustrates a geometric prism with a nine sided polygon base 205 and six circuit boards 105 arranged to form six sides of the geometric prism.

Figure 2F:
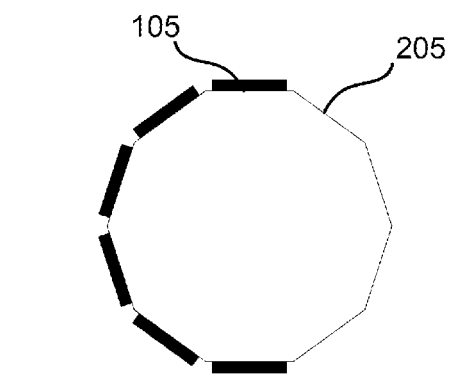

FIG. 2F illustrates another example where six circuit boards 105 are arranged to form five sides of a geometric prism with a ten sided polygon base 205. As illustrated in both examples, the six circuit boards 105 comprise at least half of the sides of the geometric prism, and wrap at least halfway around the geometric prism.

It should be understood that the number of sides of the geometric prisms illustrated in the figures are used herein for example only and the plurality of circuit boards may form geometric prisms with any number of sides. For example, a plurality of circuit boards 105 may be arranged to form sides of an 11, 12, 13, 14, 15, or more sided geometric prism. Similarly, the number of sides formed by each circuit board of the plurality of circuit boards illustrated in the figures are used herein for example only and any number of circuit boards, up to the number of sides of the geometric prism being formed, may be used. For example, a ten sided geometric prism may have 6, 7, 8, 9, or 10 sides formed by circuit boards of the plurality of circuit boards.

Figure 3:
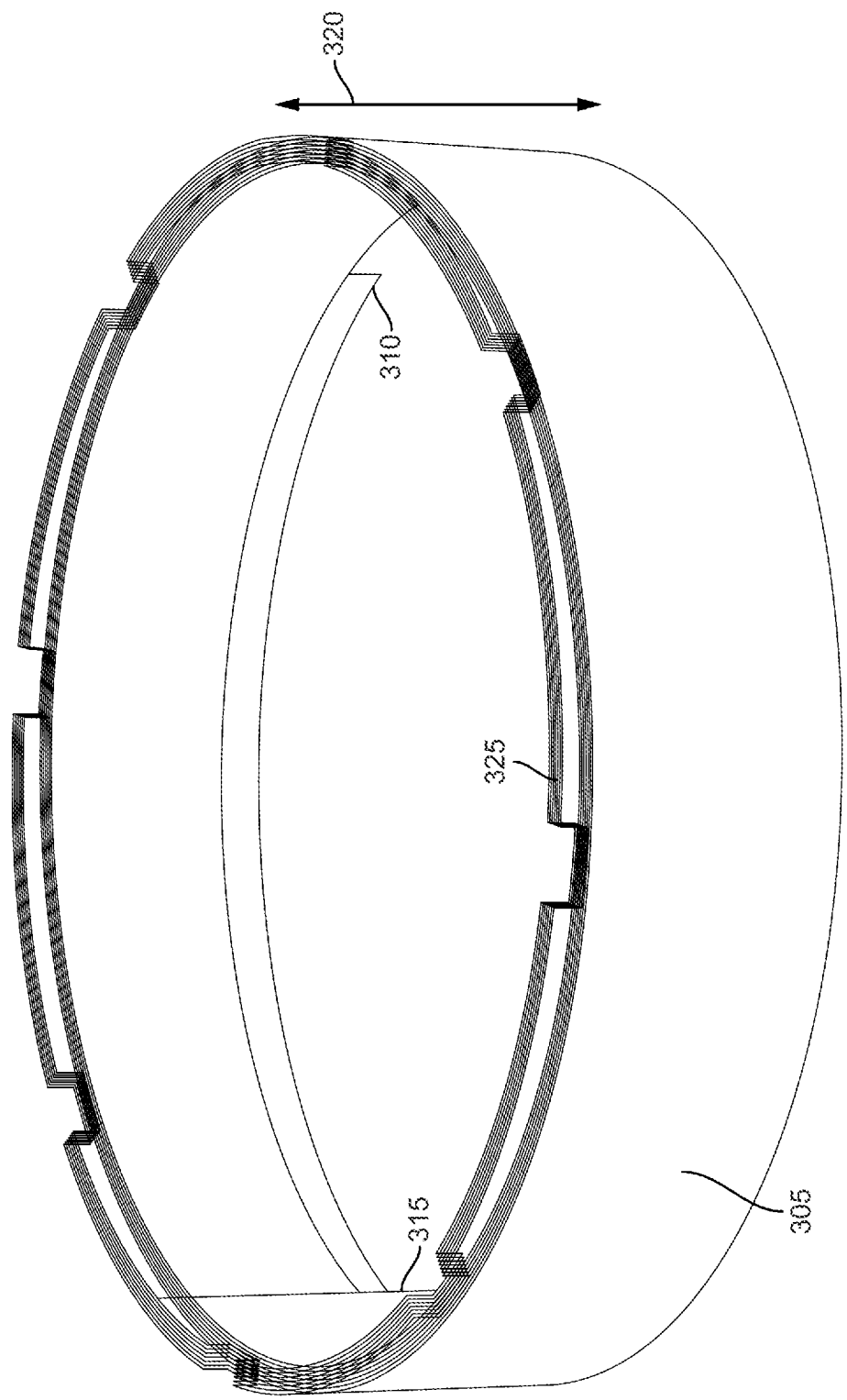
FIG. 3 illustrates a side-top view of a cylindrical power coil, according to embodiments of the present disclosure.

FIG. 3 illustrates a side-top view of a cylindrical power coil 305, according to embodiments of the present disclosure. Power coil 305 may be any type of material that is electrically conductive, such as copper, aluminum, silver, gold, graphite, or a combination of conductive materials. Power coil 305 is initially formed as a planar conducting material with a rectangular cross-section. The length of the planar conducting material is then wrapped in a spiral to form a geometric cylinder with the same height as the planar conducting material. For example, a planar conducting material with a length extending from a first end 310 to a second end 315 and height 320 is wrapped along the length of the planar conducting material in one or more turns of a spiral to form cylindrical power coil 305 with height 320 and the same number of layers 325 as the one or more turns of the spiral.

In some embodiments, power coil 305 is used for wireless power transfer. For example, a power source providing alternating current to an induction coil creates a changing magnetic field. Power coil 305 is then inductively coupled with the induction coil thereby creating an alternating electric current in power coil 305. The alternating electric current generated in power coil 305 is then used to provide power to one or more electrical components. For example, power coil 305 may be coupled to one or more circuit boards and/or electrical components, such as circuit boards 105 and or electrical components 110, as described above. The power generated by power coil 305 may then be directed to the one or more electrical components 110 in order to provide enough power to operate the one or more electrical components 110 and/or charge a battery, such as a button cell batter, as described below.

In some embodiments, power coil 305 is disposed around one or more circuit boards and/or electrical components. For example, the planar conducting material is wrapped into a cylinder with a predefined circumference. The predefined circumference is selected based on the perimeter of circuit boards 105 arranged to form sides of a geometric prism such that the predefined circumference is larger than the perimeter of the geometric prism. Alternatively or additionally, the predefined circumference may be selected to provide enough space for one or more additional components between an inner wall of power coil 305 and circuit boards 105, such as a ferrimagnetic cup, as described below.

A cylindrically wrapped power coil, such as power coil 305, reduces the overall height of an electrical device compared to more traditional pancake coils, where the conducting material is disposed within the same plane, by allowing components to be disposed within an interior of power coil 305 as opposed to above or below a traditional pancake coil. Additionally or alternatively, power coil 305 exhibits less loss at a lower total volume compared to traditional pancake coils due to the increased surface area to volume ratio provided by cylindrically wrapping a planar conducting material.

Figure 4:
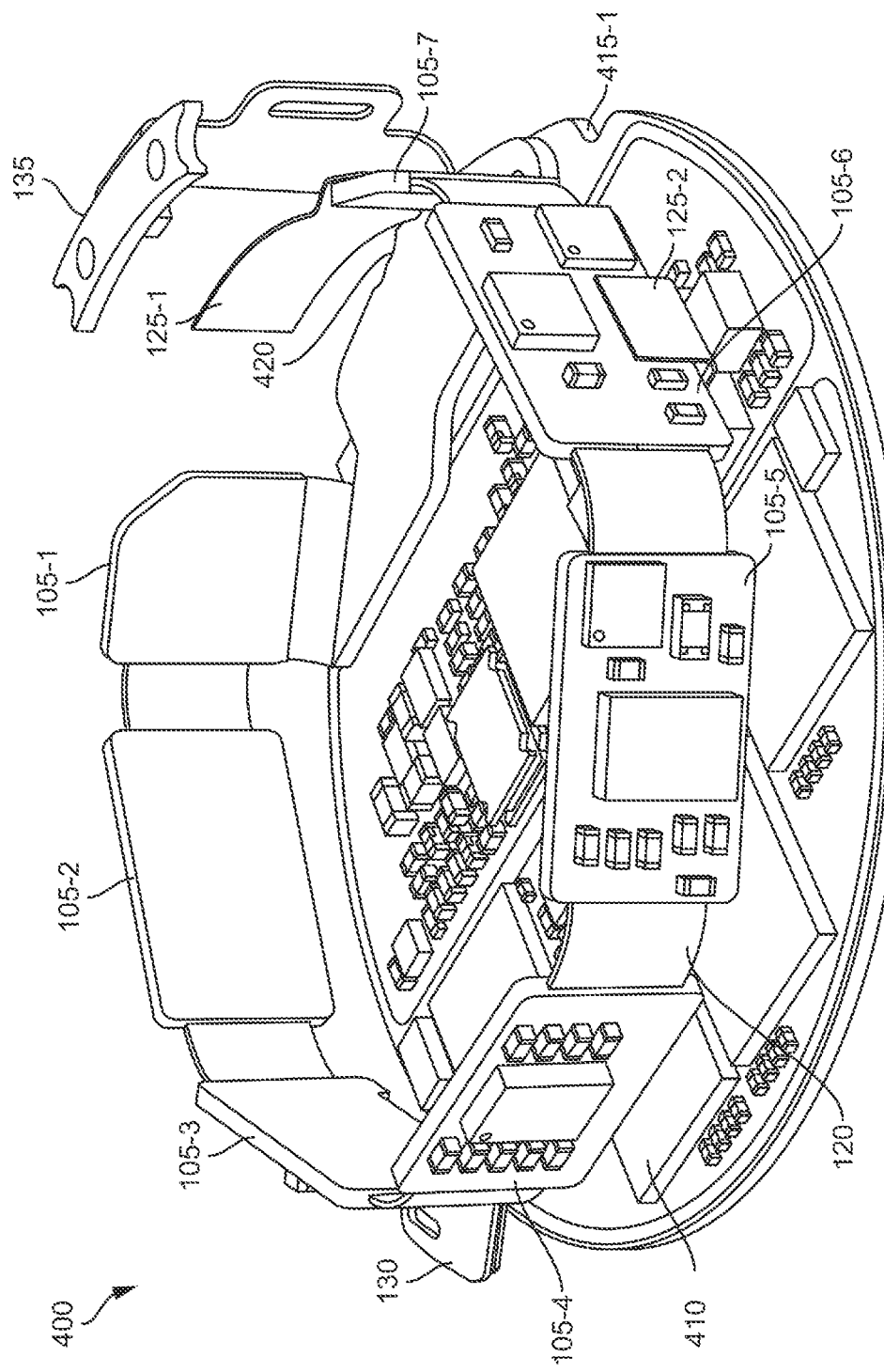
FIG. 4 illustrates a side-top view of an assembly of cylindrically wrapped electronics and a circular circuit board, according to embodiments of the present disclosure.

FIG. 4 illustrates a side-top view of an assembly 400 of cylindrically wrapped electronics and a circular circuit board, according to embodiments of the present disclosure. Assembly 400 includes a plurality of circuit boards 105 arranged in a cylindrical fashion and a circular circuit board 405. The plurality of circuit boards 105 are arranged to form sides of a geometric prism, as described above. One or more circuit boards of the plurality of circuit boards 105 include one or more connectors configured to receive power. For example, power connector 125-1 is coupled with seventh circuit board 105-7 while power connector 125-2 is coupled with sixth circuit board 105-6. One or more circuit boards of the plurality of circuit boards 105 may also be electrically coupled to a radio antenna. For example, antenna connector 135 electrically couples one or more circuit boards of the plurality of circuit boards 105 to a radio antenna, as described below.

Circular circuit board 405 is disposed parallel to a common plane that is perpendicular to each of the plurality of circuit boards 105. Circular circuit board 405 is a PCB with conductive layers separated by layers of substrate. Circular circuit board 405 may be a flexible PCB, a rigid PCB, or some combination of rigid and flexible PCB. Circular circuit board 405 includes at least one side with electrical components. For example, circular circuit board 405 includes one or more integrated circuit (IC) chips 410, such as microcontrollers, microprocessors, field programmable gate arrays (FPGAs), and/or application-specific integrated circuit (ASIC) chips. Additionally or alternatively, circular circuit board 405 may include electrical components on both sides of the circuit board. The electrical components may include any combination of resistors, capacitors, inductors, integrated circuits, transistors, ASIC chips, and/or FPGAs.

In some embodiments, circular circuit board 405 is electrically coupled to the plurality of circuit boards 105. For example, connector 420 couples circular circuit board 405 to the plurality of circuit boards 105. Connector 420 may be configured to distribute power from the plurality of circuit boards 105 to the electrical components of circular circuit board 405. Connector 420 may also be configured to transmit data between circular circuit board 405 and one or more of the plurality of circuit boards 105. Additionally or alternatively, connector 420 may couple circular circuit board 405 to a radio antenna via antenna connector 135.

Circular circuit board 405 includes one or more alignment features. For example, circular circuit board 405 includes notch 415 as a recess along the edge of circular circuit board 405. Notch 415 is configured to mate with one or more alignment features of other components of a neural implant. Circular circuit board 405 may include other notches along the edge of circular circuit board 405. Additionally or alternatively, circular circuit board 405 may include one or more other alignment features, such as openings or holes disposed across the surface of circular circuit board 405. Notch 415 may be configured to align with a corresponding bump on an enclosure, such as a ferrimagnetic cup as described below. As another example, circular circuit board 405 may have one or more alignment features configured to properly align circular circuit board 405 with connector 420 thereby aligning circular circuit board 405 with the plurality of circuit boards 105 in a predetermined orientation.

Figure 5:
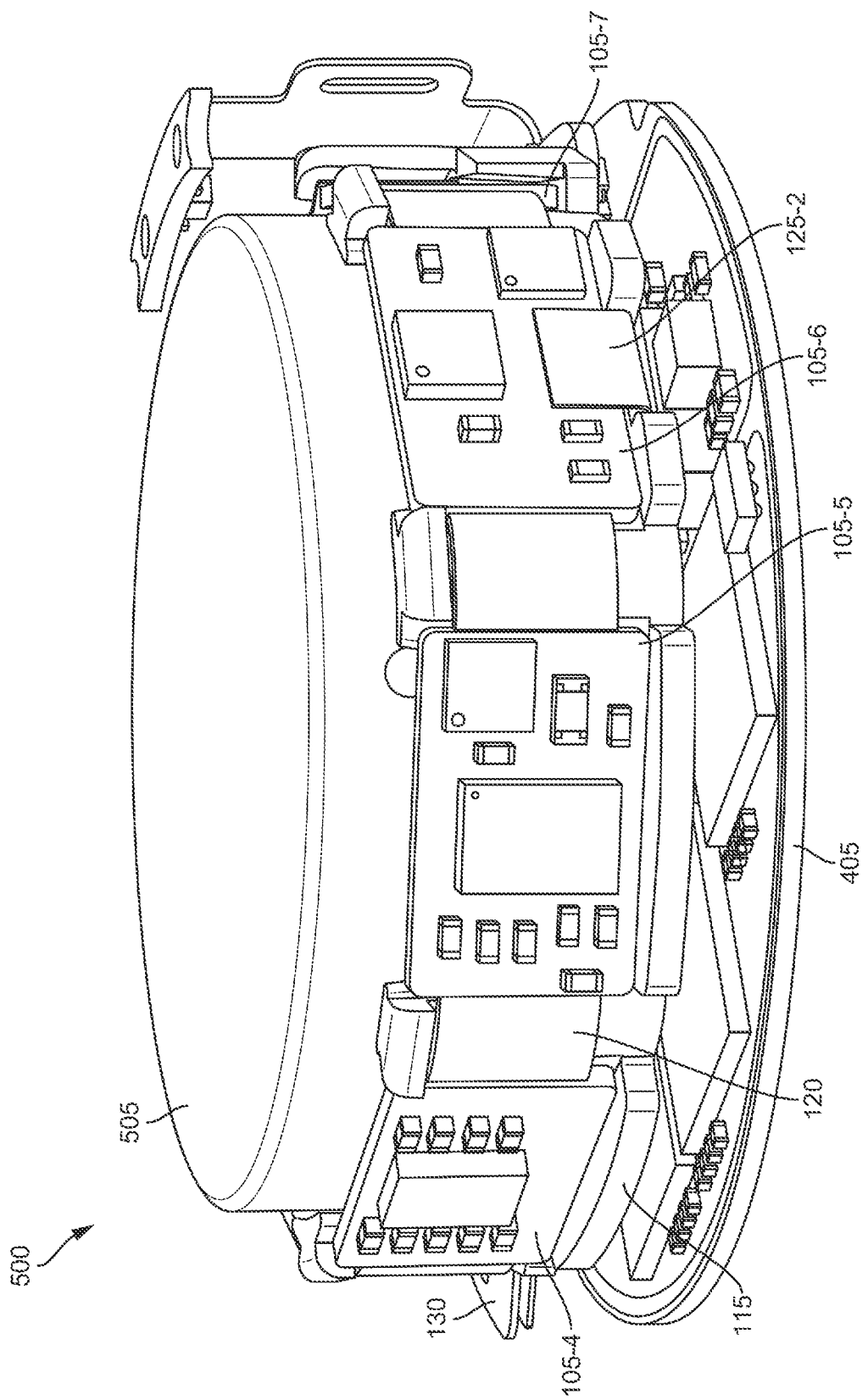
FIG. 5 illustrates a side-top view of an assembly of cylindrically wrapped electronics with a chassis, a circular circuit board, and battery, according to embodiments of the present disclosure.

FIG. 5 illustrates a side-top view of an assembly 500 of cylindrically wrapped electronics with a chassis, a circular circuit board, and battery, according to embodiments of the present disclosure. Assembly 500 includes a plurality of circuit boards 105, chassis 115, circular circuit board 405, and cylindrical button battery 505. Each circuit board of the plurality of circuit boards 105 is mechanically secured to chassis 115. Chassis 115 is configured to restrain each component of assembly 500 in a predefined position and/or orientation, such as to form the sides of a geometric prism with the plurality of circuit boards 105. Circular circuit board 405 is electrically coupled to the plurality of circuit boards 105, and disposed parallel to a common plane that is perpendicular to each of the plurality of circuit boards 105. Cylindrical button battery 505 includes a cathode casing and an anode cap.

The plurality of circuit boards 105 are arranged around cylindrical button battery 505. For example, cylindrical button battery 505 is disposed within an opening formed by the plurality of circuit boards 105 and/or an opening formed by chassis 115. The size of the opening within which cylindrical button battery 505 is disposed may be predetermined based on the circumference and/or diameter of cylindrical button battery 505. Additionally or alternatively, the size of cylindrical button battery 505 may be predetermined based on circumference and/or diameter of the opening within which cylindrical button battery 505 will be disposed. Cylindrical button battery 505 is disposed within the interior of the plurality of circuit boards 105 in a predefined orientation. The predefined orientation may be selected based on the location and/or orientation of one or more power connectors coupled to the plurality of circuit boards 105. For example, cylindrical button battery 505 may be disposed within the interior of the plurality of circuit boards 105 such that a bottom side of cylindrical button battery 505 comprising the anode cap makes contact with power connector 125-2 while the cylindrical wall of the cathode casing makes contact with power connector 125-1. Chassis 115 is further configured to support cylindrical button battery 505 and/or maintain a predefined distance between cylindrical button battery 505 and circular circuit board 405.

Cylindrical button battery 505 is configured to provide power to one or more optical components disposed on the plurality of circuit boards 105 and/or circular circuit board 405. For example, cylindrical button battery 505 distributes power via power connectors 125 to one or more of the plurality of circuit boards 105. Each circuit board of the plurality of circuit boards 105 then distributes power to an adjacent circuit board of the plurality of circuit boards 105 via one or more flex cable such, as flex cable 120. Power is then distributed to electrical components disposed on circular circuit board 405 via a connector, such as connector 420 as described above. The plurality of circuit boards 105 are also configured to distribute power received from an external power source, such as power coil 305 as described above, to cylindrical button battery 505. For example, one or more circuit boards of the plurality of circuit boards 105 receives power from a power coil via power coil connector 130. The power received from the power coil is then provided to cylindrical button battery 505 via power connectors 125.

Figure 6:
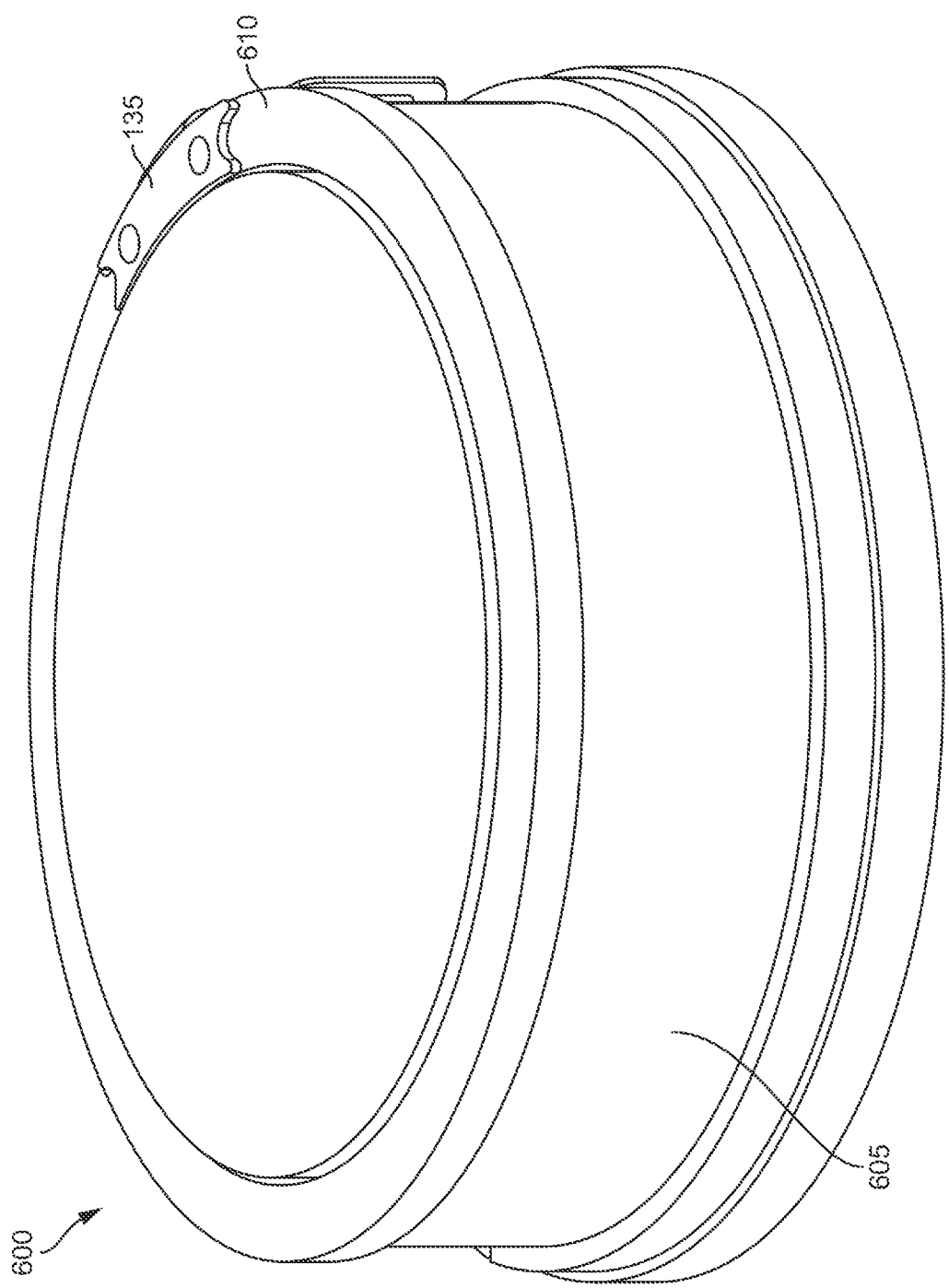
FIG. 6 illustrates a side-top view of a ferrimagnetic cup and circular loop antenna assembly, according to embodiments of the present disclosure.

FIG. 6 illustrates a side-top view of a ferrimagnetic cup and circular loop antenna assembly 600, according to embodiments of the present disclosure. Assembly 600 includes ferrimagnetic cup 605 and radio antenna 610. Ferrimagnetic cup 605 may be composed of sintered ferrite. The sintered ferrite may be composed of one or more ceramic and/or metallic compounds. As illustrated, ferrimagnetic cup 605 has cylindrical sidewalls, a planar base on one end of the cylindrical sidewalls, an opening opposite the planar base, and a substantially hollow interior.

Assembly 600 may also include a plurality of circuit boards and a button cell battery. Ferrimagnetic cup 605 is configured to have one or more components disposed within the interior of ferrimagnetic cup 605. For example, the plurality of circuit boards 105 secured to chassis 115, circular circuit board 405, and/or cylindrical button battery 505 of assembly 500, as discussed above, may be disposed within the interior of ferrimagnetic cup 605. Arranging one or more of the components within ferrimagnetic cup 605 reduces eddy current loss in the components, such as a metallic battery casing of cylindrical button battery 505 and/or other electronic copper planes.

The inner circumference and/or diameter of the cylindrical sidewalls of ferrimagnetic cup 605 may be selected based on the circumference, diameter and/or volume of the components to be disposed within ferrimagnetic cup 605. For example, the inner circumference of a cylindrical sidewall of ferrimagnetic cup 605 may be based on the circumference of a geometric prism formed by the plurality of circuit boards 105, as described above, such that each of the plurality of circuit boards 105 may fit within ferrimagnetic cup 605 with the sides of each of the plurality of circuit boards 105 facing the cylindrical side wall. As another example, the inner circumference of a cylindrical sidewall may be based on the circumference of circular circuit board 405, as described above, such that circular circuit board 405 may fit within the opening and be parallel with the planar base.

Ferrimagnetic cup 605 is further configured to shield the one or more components disposed within the interior of ferrimagnetic cup 605 from external electromagnetic interference (EMI). Sources of external EMI may include a power coil, such as power coil 305 as further described below, and/or radio antenna 610. Additionally or alternatively, ferrimagnetic cup 605 functions as a shield for internal sources of EMI from within the interior of ferrimagnetic cup 605. For example, ferrimagnetic cup 605 may shield EMI produced by the plurality of circuit boards 105 and/or circular circuit board 405 from interfering with the functionality of radio antenna 610 and/or leaking into a patient's neural pathways.

Radio antenna 610 forms a circular loop with a circumference in a first plane. The first plane of radio antenna 610 is parallel with the planar base of ferrimagnetic cup 605. As illustrated, radio antenna 610 is arranged on an exterior surface of ferrimagnetic cup 605 such that the circular loop formed by radio antenna 610 wraps around a circumference of the planar base and/or is substantially coplanar with the planar base. Forming radio antenna 610 as a circular loop and arranging it on an exterior surface of ferrimagnetic cup 605 serves to reduce the overall height of a resulting neural implant. Additionally or alternatively, the large diameter formed by radio antenna 610 may produce better average gain with a more uniform beam pattern as compared with other antenna designs.

In some embodiments, radio antenna 610 is electrically coupled to one or more of the plurality of circuit boards 105, as described above. For example, radio antenna 610 is connected to antenna connector 135 on the exterior of ferrimagnetic cup 605. Antenna connector 135 may then connect with one or more of the plurality of circuit boards 105 and/or circular circuit board 405 within the interior of ferrimagnetic cup 605. Electrically coupling radio antenna 610 to one or more of the plurality of circuit boards 105 and/or circular circuit board 405 may enable one or more electrical components to transmit and/or receive wireless data between the electrical components and one or more devices outside of the neural implant.

Figure 7:
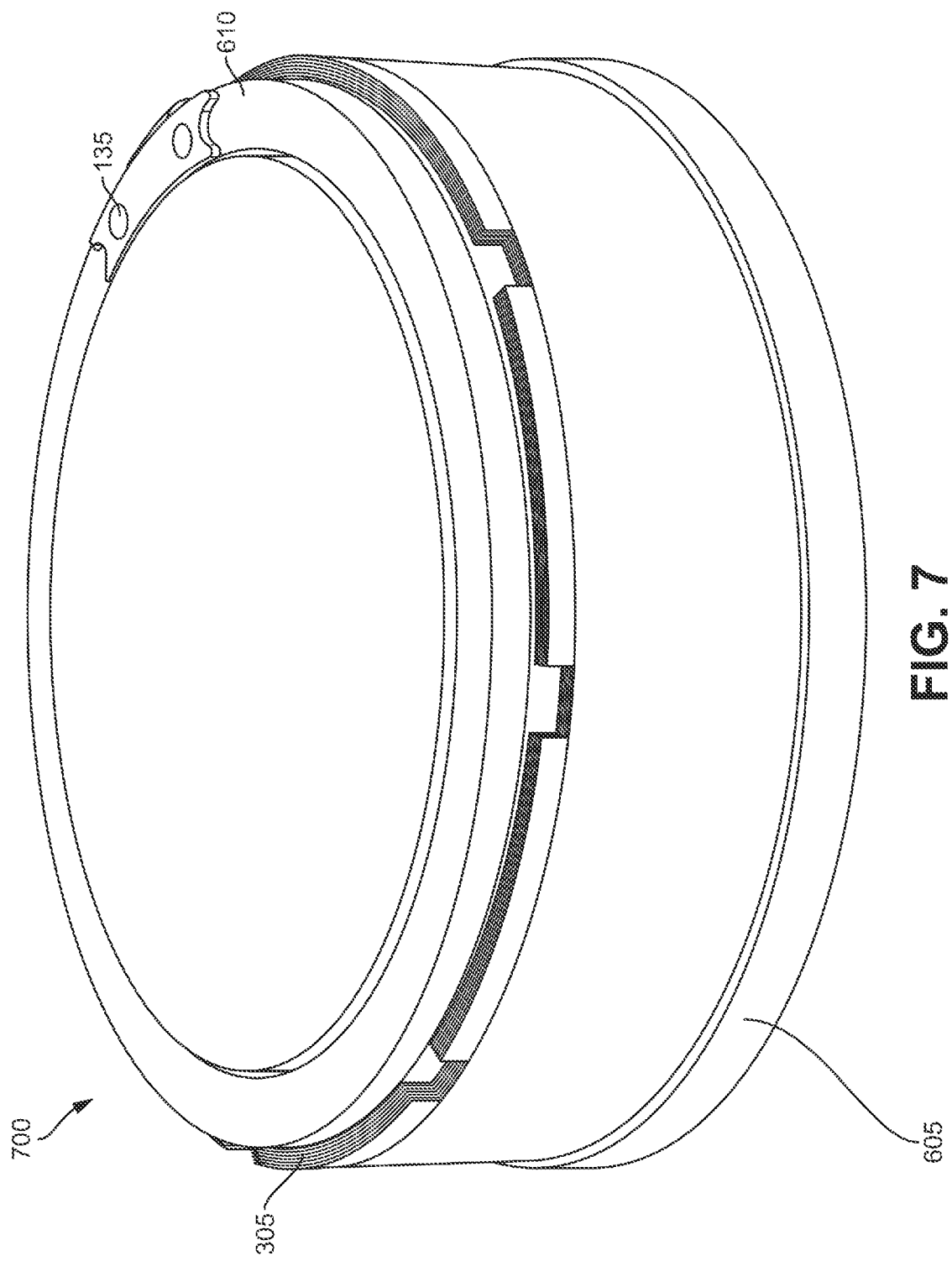
FIG. 7 illustrates a side-top view of a ferrimagnetic cup, circular loop antenna, and cylindrical power coil assembly, according to embodiments of the present disclosure.

FIG. 7 illustrates a side-top view of a ferrimagnetic cup, circular loop antenna, and cylindrical power coil assembly 700, according to embodiments of the present disclosure. Assembly 700 includes ferrimagnetic cup 605, radio antenna 610, and power coil 305. In some embodiments, assembly 700 is formed by disposing a power coil, such as power coil 305 as described above, around a cylindrical sidewall of ferrimagnetic cup 605. In some embodiments, ferrimagnetic cup 605 is disposed within the geometric cylinder formed by power coil 305, thereby separating power coil 305 from any components within the interior of ferrimagnetic cup 605, such as the plurality of circuit boards 105 and/or circular circuit board 405. Separating power coil 305 from the plurality of circuit boards 105 and/or circular circuit board 405 may reduce EMI caused by inductive coupling between power coil 305 and an external induction coil.

The diameter and/or circumference of power coil 305 may be selected based on the outer diameter and/or circumference of ferrimagnetic cup 605. For example, the circumference of power coil 305 may be selected to provide a predetermined distance between the external surface of the cylindrical sidewall of ferrimagnetic cup 605 and the internal layer of power coil 305. Alternatively, the circumference of power coil 305 may be selected to provide contact between the internal layer of power coil 305 and the external surface of the cylindrical sidewall of ferrimagnetic cup 605.

One or more components disposed within ferrimagnetic cup 605 are electrically coupled to power coil 305 disposed around the exterior of ferrimagnetic cup 605. For example, one or more of the plurality of circuit boards 105 may be electrically coupled via power coil connector 130 with power coil 305, as described above. Power connector 130 may extend from the interior of ferrimagnetic cup 605, through an opening of ferrimagnetic cup 605, to the exterior of ferrimagnetic cup 605 in order to make contact with power coil 305. The opening for power coil connector 130 may be located at and/or near the opening opposite the planar base of ferrimagnetic cup 605. For example, a portion of the cylindrical sidewall of ferrimagnetic cup may be removed to allow for power coil connector 130 to extend therethrough.

Figure 8:
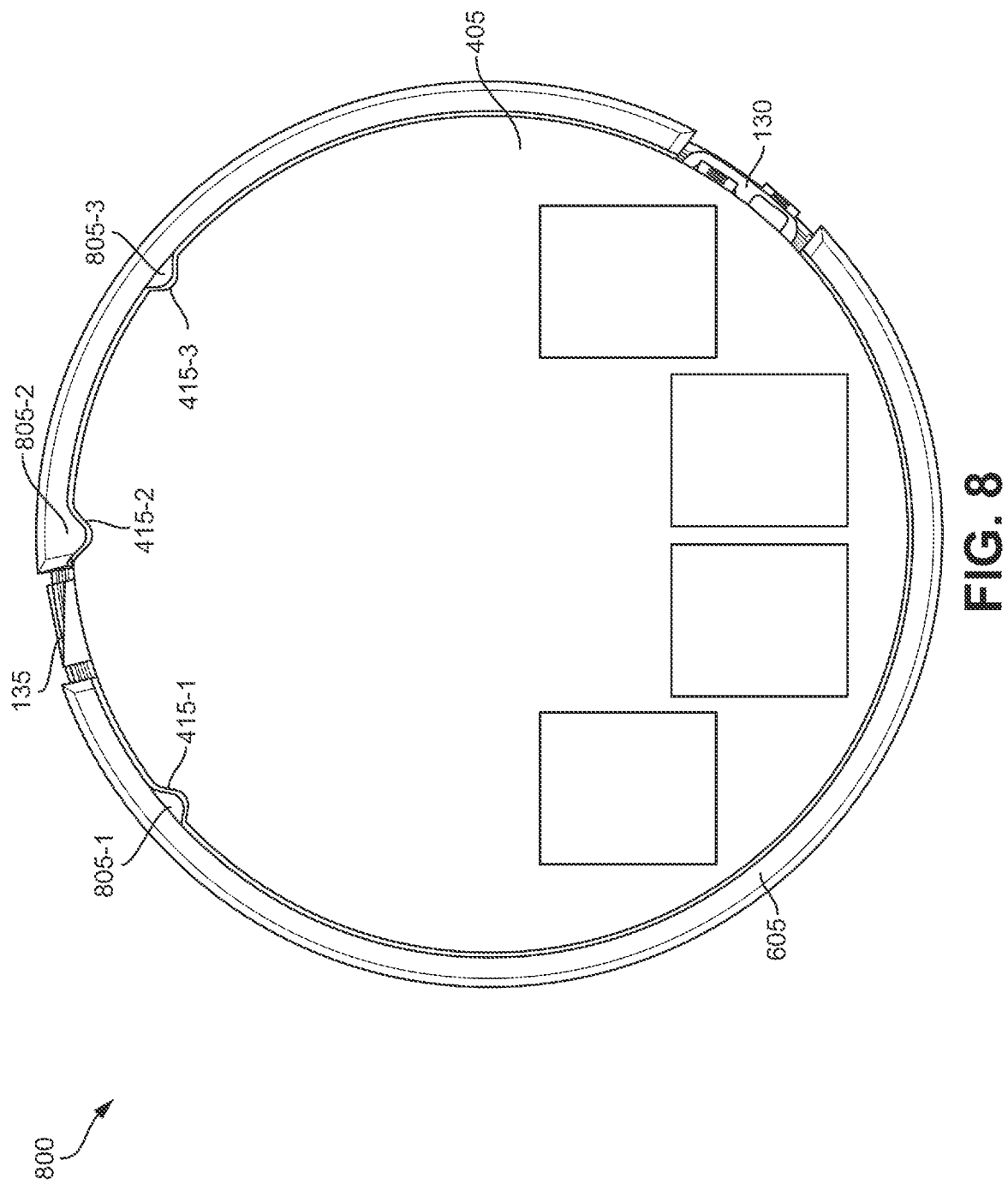
FIG. 8 illustrates a bottom view of a ferrimagnetic cup and circular circuit board assembly including alignment features, according to embodiments of the present disclosure.

FIG. 8 illustrates a bottom view of a ferrimagnetic cup and circular circuit board assembly 800 including alignment features, according to embodiments of the present disclosure. Assembly 800 includes ferrimagnetic cup 605 and circular circuit board 405. Additionally or alternatively, assembly 800 can include a plurality of circuit boards and a button cell battery, such as the plurality of circuit boards 105 and/or cylindrical button battery 505 described above. For example, the plurality of circuit boards 105 and cylindrical button battery 505 may be disposed nearer to the planar base of ferrimagnetic cup 605 while circular circuit board 405 is disposed within the opening opposite the planar base.

Ferrimagnetic cup 605 includes one or more openings in the cylindrical side wall to allow one or more connectors to extend from within the interior of ferrimagnetic cup 605 to the exterior of ferrimagnetic cup 605. For example, ferrimagnetic cup 605 includes an opening for antenna connector 135. As another example, ferrimagnetic cup 605 includes an opening for power coil connector 130.

Ferrimagnetic cup 605 also includes one or more alignment features. The one or more alignment features bumps 805 on the interior surface of ferrimagnetic cup 605. The one or more alignment features may have predetermined sizes and/or dimensions based on corresponding alignment features on one or more components to be disposed within the interior of ferrimagnetic cup 605. For example, bump 805-2 is approximately the same size and/or dimensions as notch 415-2 of circular circuit board 405. As another example, bump 805-1 and bump 805-3 are approximately the same size and/or dimensions as one or more notches of chassis 115, such as notch 150 as described above.

Placing the one or more alignment features at predetermined locations and/or in predetermined orientations configures ferrimagnetic cup 605 to align one or more components within the interior of ferrimagnetic cup 605. For example, bump 805-1 and/or bump 805-3 configure ferrimagnetic cup 605 to align chassis 115 in a predefined orientation within the interior of ferrimagnetic cup 605. The plurality of circuit boards 105 may be secured to chassis 115 as described above, and thereby maintained in a predefined orientation within ferrimagnetic cup 605. As another example, bump 805-2 configures ferrimagnetic cup 605 to line up with notch 415-2 of circular circuit board 405, thereby aligning circular circuit board 405 within the opening of ferrimagnetic cup 605 and parallel with the planar base of ferrimagnetic cup 605.

Figure 9:
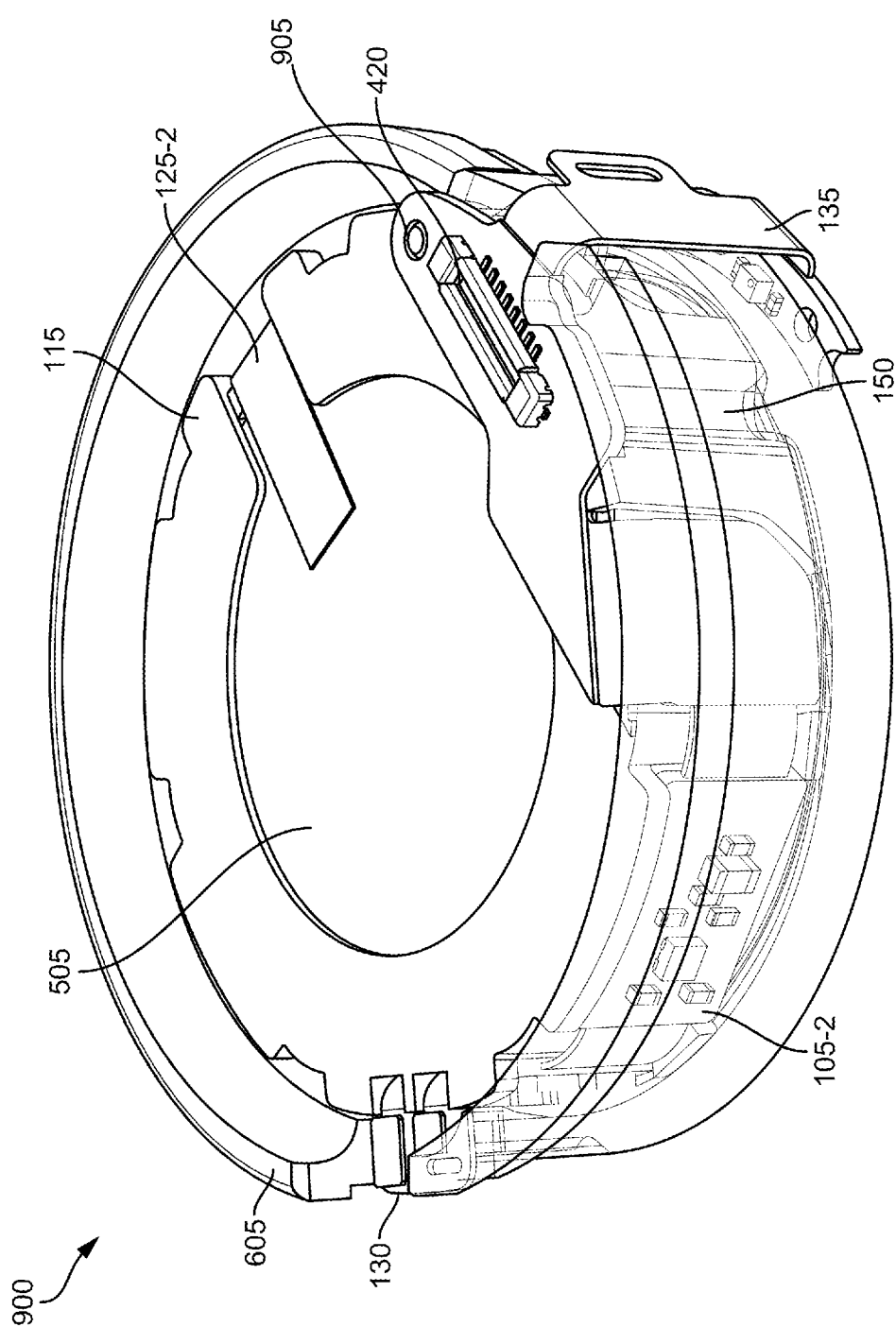
FIG. 9 illustrates a side-bottom cutaway view of an assembly of a ferrimagnetic cup and cylindrically wrapped electronics including alignment features, according to embodiments of the present disclosure.

FIG. 9 illustrates a side-bottom cutaway view of an assembly 900 of a ferrimagnetic cup and cylindrically wrapped electronics including alignment structures, according to embodiments of the present disclosure. Assembly 900 includes a plurality of circuit boards 105, chassis 115, cylindrical button battery 505, and/or ferrimagnetic cup 605. The plurality of circuit boards 105 are arranged to form sides of a five or greater sided geometric prism. One or more of the plurality of circuit boards 105 are mechanically secured to chassis 115. Chassis 115 is configured to restrain the plurality of circuit boards 105 in the form of geometric prism. The plurality of circuit boards 105 secured to chassis 115 are arranged within the interior of ferrimagnetic cup 605 such that the sides of the plurality of circuit boards 105 with electrical components face the cylindrical side wall of ferrimagnetic cup 605. For example, circuit board 105-2 faces the cylindrical side wall of ferrimagnetic cup 605 and is perpendicular to the planar base of ferrimagnetic cup 605.

The plurality of circuit boards 105 are arranged around cylindrical button battery 505. For example, cylindrical button battery 505 is disposed within the interior of the geometric prism formed by the plurality of circuit boards 105 and/or by chassis 115. Cylindrical button battery 505 is disposed within the interior of the plurality of circuit boards 105 in a predefined orientation. The predefined orientation is selected based on the location and/or orientation of one or more power connectors coupled to the plurality of circuit boards 105. For example, cylindrical button battery 505 is disposed within the interior of the plurality of circuit boards 105 such that a bottom side of cylindrical button battery 505, visible in the figure, comprising the anode cap makes contact with power connector 125-2 while the cylindrical wall of the cathode casing makes contact with power connector 125-1. Chassis 115 is further configured to support cylindrical button battery 505.

In some embodiments, assembly 900 also includes a circular circuit board, such as circular circuit board 405 as described above, electrically coupled to the plurality of circuit boards 105. Circular circuit board 405 may be disposed parallel to a common plane that is perpendicular to each of the plurality of circuit boards 105. Circular circuit board 405 may be coupled to the plurality of circuit boards 105 via a connector 420, as described above. Connector 420 is configured to distribute power from the plurality of circuit boards 105 to the electrical components of circular circuit board 405. Connector 420 is also configured to transmit data between circular circuit board 405 and one or more of the plurality of circuit boards 105.

In some embodiments, assembly 900 also includes a power coil, such as power coil 305 as described above, disposed around the exterior surface of the cylindrical sidewall of ferrimagnetic cup 605. One or more components disposed within ferrimagnetic cup 605 are electrically coupled to power coil 305. For example, one or more of the plurality of circuit boards 105 are electrically coupled via power coil connector 130 with power coil 305. Power connector 130 extends from the interior of ferrimagnetic cup 605, through an opening of the cylindrical sidewall of ferrimagnetic cup 605, to the exterior of ferrimagnetic cup 605 in order to make contact with power coil 305.

In some embodiments, assembly 900 also includes a power coil, such as radio antenna 610 as described above, arranged on an exterior surface of ferrimagnetic cup 605 such that the circular loop formed by radio antenna wraps around a circumference of the planar base and/or is substantially coplanar with the planar base. Radio antenna 610 is electrically coupled to one or more of the plurality of circuit boards 105. For example, radio antenna 610 is connected to antenna connector 135 on the exterior of ferrimagnetic cup 605. Antenna connector is then coupled with one or more of the plurality of circuit boards 105 and/or circular circuit board 405 within the interior of ferrimagnetic cup 605.

One or more components of assembly 900 include alignment features. Alignment features configure the one or more components of assembly 900 to be arranged in a predefined orientation within the ferrimagnetic cup. Alignment features may include bumps, protrusions, holes, notches, or any similarly suitable physical structure configured to mate with a corresponding physical structure in a predefined orientation. For example, notch 150 of chassis 115 is configured to mate with a bump on ferrimagnetic cup 605, such as bump 805-3 as described above. When inserting chassis 115 into ferrimagnetic cup 605, notch 150 and bump 805-3 mate with each other to ensure that chassis 115 is installed within ferrimagnetic cup 605 according to a predetermined orientation. As another example, chassis 115 includes bump 905 on the circular base configured to mate with a hole or opening of connector 420.

Figure 10:
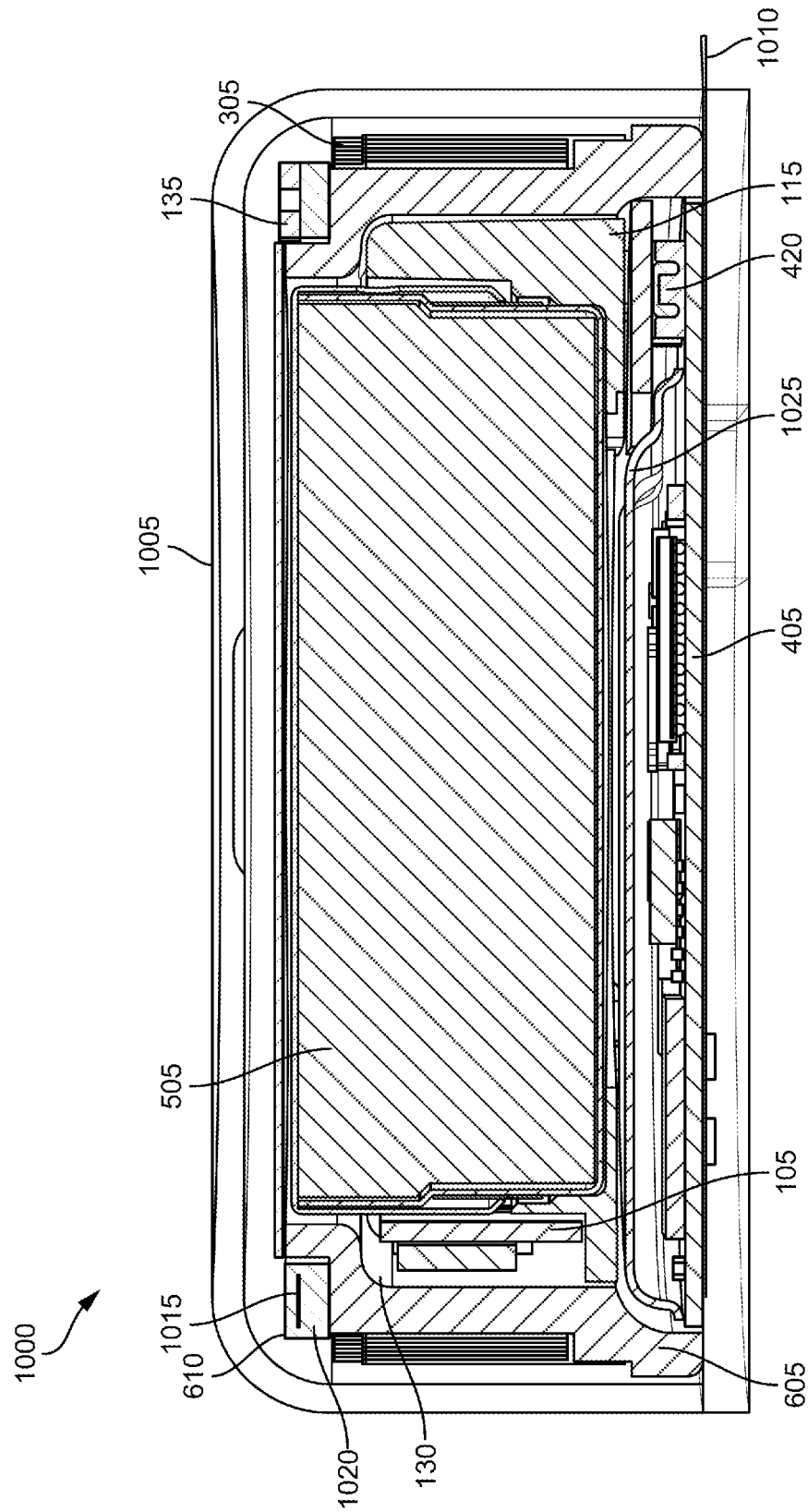
FIG. 10 illustrates a vertical cross section of a high density neural implant, according to embodiments of the present disclosure.

FIG. 10 illustrates a vertical cross section of a high density neural implant 1000, according to embodiments of the present disclosure. Neural implant 1000 includes a plurality of circuit boards 105, chassis 115, power coil 305, circular circuit board 405, cylindrical button battery 505, ferrimagnetic cup 605, radio antenna 610, and/or housing 1005. Housing 1005 may be composed of any body-safe material designed for placement within the human body. In some embodiments, housing 1005 is cylindrical in shape with two planar ends and a cylindrical sidewall. The diameter of the planar ends may be larger than the height of the cylindrical sidewall. The height of housing 1005 may be selected in order to maximize efficiency while reducing the concerns of tissue erosion potentially caused by neural implant 1000. Housing 1005 forms the external surface of neural implant 1000 and encloses one or more of the remaining components of neural implant 1000 within an interior of housing 1005. In some embodiments, housing 1005 includes one or more openings for electrical leads to pass from an interior of housing 1005 to the exterior of housing 1005. For example, electrical leads 1010 passes through an opening of housing 1005 and into tissue surrounding neural implant 1000. Electrical leads 1010 are configured to transmit and/or receive electrical impulses between the surrounding tissue and one or more components of neural implant 1000, such as circular circuit board 405.

Ferrimagnetic cup 605 is disposed within the interior of housing 1005. As illustrated, the cylindrical sidewalls of ferrimagnetic cup 605 are parallel with the cylindrical sidewall of housing 1005 while the planar base and opening opposite the planar base of ferrimagnetic cup 605 are parallel with the planar ends of housing 1005. The distance between the cylindrical sidewalls of ferrimagnetic cup 605 and the cylindrical sidewall of housing 1005 are a predetermined distance. For example, the external circumference of the cylindrical sidewall nearest the opening of ferrimagnetic cup 605 is selected to provide contact between the cylindrical sidewall and housing 1005. Selecting an external circumference that provides contact between the cylindrical sidewall and housing 1005 stabilizes ferrimagnetic cup 605 within housing 1005 and reduce unwanted movement of ferrimagnetic cup 605 relative to housing 1005. As another example, the external circumference of one or more other cylindrical sidewalls of ferrimagnetic cup 605 are selected to provide space for one or more components to be arranged between ferrimagnetic cup 605 and the interior surface of housing 1005, such as power coil 305 and/or radio antenna 610.

Power coil 305 is disposed within the interior of housing 1005 such that the planar conducting material of power coil 305 is parallel with the cylindrical sidewall of housing 1005 and/or a cylindrical sidewall of ferrimagnetic cup 605. Additionally or alternatively, radio antenna 610 is disposed within an interior of housing 1005 such that the circumference of the circular loop formed by radio antenna 610 is in a first plane parallel with the planar ends of housing 1005 and/or the planar base of ferrimagnetic cup 605. Radio antenna 610 is disposed around the cylindrical sidewall of ferrimagnetic cup 605 closest to the planar base of ferrimagnetic cup 605. As further illustrated, radio antenna 610 includes a conductor 1015 disposed within dielectric substrate 1020. Power coil 305 and/or radio antenna 610 are electrically coupled to at least one circuit board of the plurality of circuit boards 105. For example, radio antenna 610 is coupled with a circuit board, such as circuit board 105, via antenna connector 135.

The plurality of circuit boards 105 are arranged in a cylindrical fashion within the interior of housing 1005 and/or within the interior of ferrimagnetic cup 605. For example, a plurality of at least four circuit boards 105 are arranged to form sides of a five or greater sided geometric prism. The sides of the geometric prism correspond to the polygon base of the geometric prism, such that the geometric prism has the same number of sides as the polygon base. The polygon base is perpendicular to the sides of the geometric prism and forms a common plane. The common plane is parallel to the planar ends of housing 1005 and/or the planar base of ferrimagnetic cup 605. Each of the plurality of circuit boards 105 are perpendicular to the common plane formed by the polygon base of the geometric prism. In some embodiments, the plurality of circuit boards 105 makes up at least half of the sides of the five or greater sided geometric prism, such that the circuit boards wrap at least halfway around the geometric prism, an interior circumference of housing 1005, and/or an interior circumference of ferrimagnetic cup 605.

One or more circuit boards of the plurality of circuit boards 105 are mechanically secured to chassis 115. Chassis 115 is configured to restrain one or more circuit boards of the plurality of circuit boards 105 in a predefined position and/or orientation, such as to form the sides of a geometric prism with the plurality of circuit boards 105. The distance between the widest points around the outer circumference of chassis 115 and an interior surface of ferrimagnetic cup 605 may be a predetermined distance. For example, chassis 115 may be configured to provide contact and/or a maximum clearance between the widest points around the outer circumference of chassis 115 and an interior sidewall of ferrimagnetic cup 605. Configuring chassis 115 to provide contact with ferrimagnetic cup 605 stabilizes chassis 115 within ferrimagnetic cup 605 and reduces unwanted movement of chassis 115 relative to ferrimagnetic cup 605. Additionally or alternatively, chassis 115 and/or ferrimagnetic cup 605 include one or more alignment features configured to align chassis 115 within ferrimagnetic cup 605 in a predetermined position and/or orientation, as described above.

Cylindrical button battery 505 is disposed within the interior of housing 1005, ferrimagnetic cup 605, and/or the plurality of circuit boards 105. For example, cylindrical button battery 505 is disposed within an opening formed by the plurality of circuit boards 105 and/or an opening formed by chassis 115. The size of the opening within which cylindrical button battery 505 is disposed is predetermined based on the circumference and/or diameter of cylindrical button battery 505. For example, the interior circumference of chassis 115 is configured to maintain contact between cylindrical button battery 505 and one or more power connectors, such as power connectors 125 as described above.

Circular circuit board 405 is disposed within the interior of housing 1005 and/or ferrimagnetic cup 605. For example, circular circuit board 405 is disposed within the opening of ferrimagnetic cup 605 opposite the planar base of ferrimagnetic cup 605. Circular circuit board is also disposed parallel to the common plane formed by the polygon base of the plurality of circuit boards 105, the planar base of ferrimagnetic cup 605, and/or the planar ends of housing 1005. Circular circuit board 605 is electrically coupled to one or more of the plurality of circuit boards 105. For example, circular circuit board 405 is coupled to the plurality of circuit boards 105 via connector 420. Connector 420 is configured to distribute power from the plurality of circuit boards 105 to one or more electrical components of circular circuit board 405. Connector 420 is also configured to transmit data between circular circuit board 405 and one or more of the plurality of circuit boards 105. Additionally or alternatively, connector 420 couples circular circuit board 405 to radio antenna 610 via antenna connector 135.

Neural implant 1000 also includes metallic shield 1025 connected to circular circuit board 405. Metallic shield 1025 may be made from one or more metallic compounds and is configured to reduce the effects of EMI on the one or more electronic components of circular circuit board 405 from one or more other components of neural implant 1000, such as power coil 305, radio antenna 610, cylindrical button battery 505, and/or the plurality of circuit boards 105. Metallic shield 1025 is continuously connected around a circumference of circular circuit board 405. For example, the entire edge of metallic shield 1025 may be soldered, glued, or otherwise connected to circular circuit board. The continuous connection between metallic shield 1025 and circular circuit board 405 acts as a humidity barrier, thereby reducing the potential for unwanted humidity accumulation in and around one or more of the electrical components of circular circuit board 405.

Figure 11:
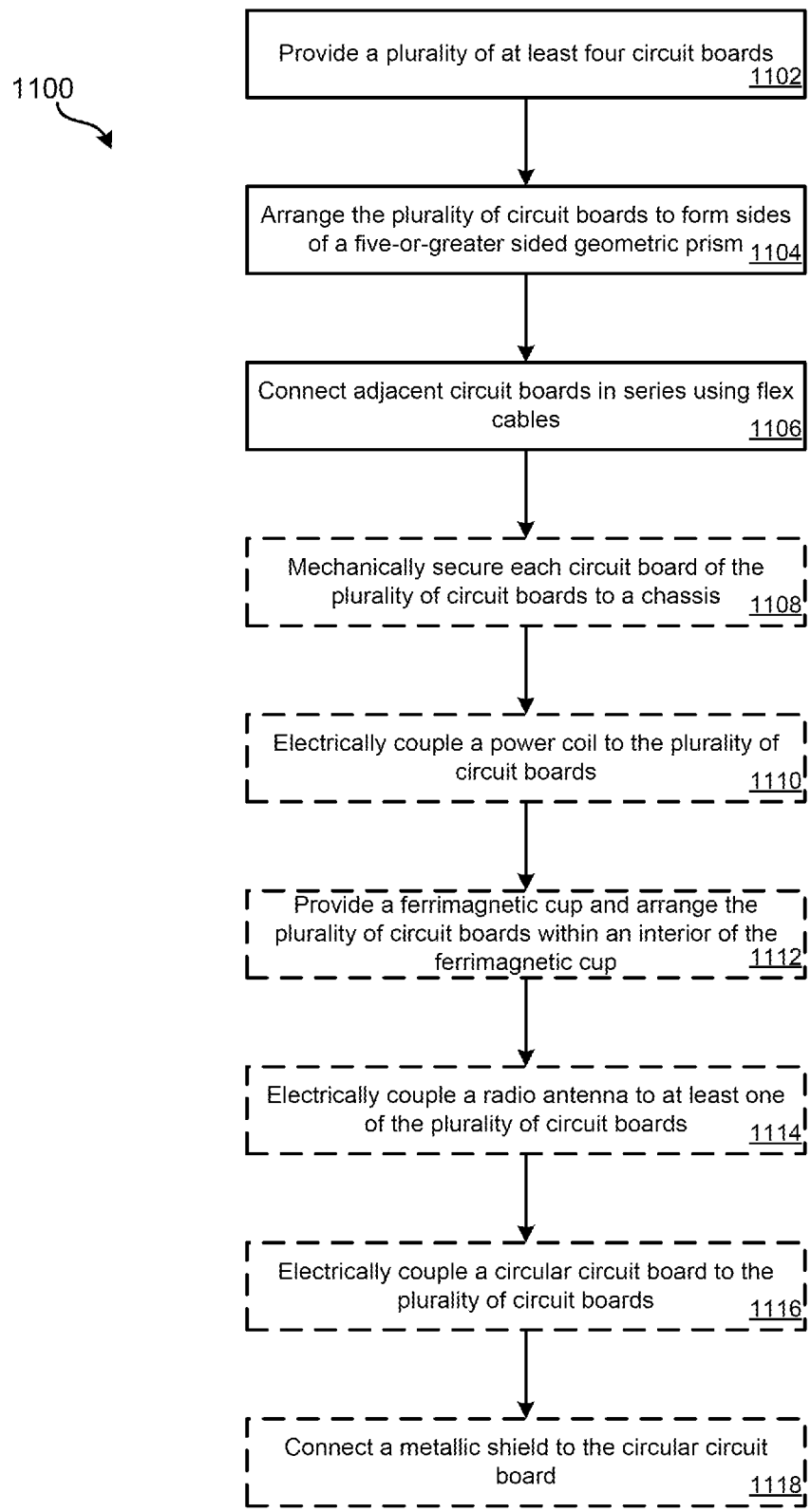
FIG. 11 is a flowchart illustrating a method 1100 of manufacturing a space-saving, wrapped cylindrical electronic apparatus, according to embodiments of the present disclosure.

FIG. 11 is a flowchart illustrating a method 1100 of manufacturing a space-saving, wrapped cylindrical electronic apparatus according to embodiments of the present disclosure. The resulting wrapped cylindrical electronic apparatus may be a neural and/or other surgical implant configured for placement within a human body. Although depicted as various manufacturing steps occurring in a particular sequence or order, this is not intended to be limiting. In certain alternative embodiments, the steps may be performed in some different order or some steps may also be performed in parallel. In certain embodiments, the components discussed in connection with the depicted method may be the same or be configured in a similar manner as the components described above.

Method 1100 includes, at block 1102, providing a plurality of at least four circuit boards. Each circuit board of the plurality of circuit boards may be a printed circuit board (PCB) with one or more conductive layers separated by one or more layers of substrate. Each circuit board of the plurality of circuit boards may be a flexible PCB, a rigid PCB, or some combination of rigid and flexible PCB. One or more of the plurality of circuit boards may include at least one side with electrical components. Additionally or alternatively, one or more of the plurality of circuit boards may include electrical components on both sides of the circuit board. The electrical components may include any combination of resistors, capacitors, inductors, integrated circuits, transistors, and/or sensors. At least one circuit board of the plurality of circuit boards may include a connector configured to receive power, such as connectors 125 as described above.

At block 1104, the plurality of circuit boards are arranged to form sides of a five-or-greater sided geometric prism. The sides of the geometric prism correspond to the polygon base of the geometric prism, such that the geometric prism has the same number of sides as the polygon base. The polygon base may be perpendicular to the sides of the geometric prism and form a common plane. Each of the plurality of circuit boards may be perpendicular to the common plane formed by the polygon base of the geometric prism. In some embodiments, the plurality of circuit boards makes up at least half of the five or greater sided geometric prism, such that the circuit boards wrap at least halfway around the geometric prism.

At block 1106, adjacent circuit boards of the plurality of circuit boards are connected in series using flex cables. The flex cables may distribute power received from a power connector, such as power connector 125-1 as described above, to each circuit board of the plurality of circuit boards in series. The one or more flex cables may also transmit data between adjacent circuit boards.

At block 1108, each circuit board of the plurality of circuit boards is optionally mechanically secured to a chassis. The chassis can be made from any rigid and/or semi rigid material, such as plastic. The chassis may be configured to restrain the plurality of circuit boards in a predefined position and/or orientation, such as to form the sides of the geometric prism. The chassis may include one or more support structures with connection points for each circuit board of the plurality of circuit boards such that when the plurality of circuit boards are mechanically connected to the connection points, the plurality of circuit boards form sides of the geometric prism. The chassis may also include one or more surfaces between the connection points such that when the plurality of circuit boards are mechanically connected to the connection points, the one or more surfaces maintain a predefined bend radii of the flex cables between each circuit board of the plurality of circuit boards.

At block 1110, a power coil is optionally electrically coupled to the plurality of circuit boards. Power coil 305 may initially be formed as a planar conducting material with a rectangular cross-section. The length of the planar conducting material may then be wrapped in a spiral around the geometric prism formed by the plurality of circuit boards to form a geometric. The power coil may be used for wireless power transfer. For example, a power source may provide alternating current to an induction coil creating a changing magnetic field. The power coil may then be inductively coupled with the induction coil thereby creating an alternating electric current in the power coil. The alternating electric current generated in the power coil may then be used to provide power to the electrical components of the plurality of circuit boards. Additionally or alternatively, the power generated by power coil may provide power to charge a battery. In some embodiments, method 1100 may optionally include electrically coupling a cylindrical button battery, such as cylindrical button battery 505 as described above, to the power coil and/or the plurality of circuit boards.

At block 1112, a ferrimagnetic cup is optionally provided and the plurality of circuit boards are optionally arranged within an interior of the ferrimagnetic cup. The ferrimagnetic cup may have cylindrical sidewalls, a planar base on one end of the cylindrical sidewalls, an opening opposite the planar base, and have a substantially hollow interior. The plurality of circuit boards, optionally secured to the chassis as described above, may be disposed within the interior of the ferrimagnetic cup. The plurality of circuit boards may be arranged in a cylindrical fashion within the interior of ferrimagnetic cup such that the common plane of the plurality of circuit boards is parallel to the planar base of the ferrimagnetic cup, and the sides of the plurality of circuit boards with electrical components face the cylindrical sidewall of the ferrimagnetic cup.

At block 1114, a radio antenna is optionally electrically coupled to the plurality of circuit boards. The radio antenna may form a circular loop with a circumference in a first plane. The circular loop formed by the radio antenna may be arranged adjacent to the plurality of circuit boards such that the first plane formed by the radio antenna is parallel to the common plane of the plurality of circuit boards. The radio antenna may optionally be separated from the plurality of circuit boards by the ferrimagnetic cup. For example, the radio antenna may be arranged on an exterior surface of the ferrimagnetic cup such that the circular loop formed by radio antenna wraps around a circumference of the planar base and/or is substantially coplanar with the planar base, as described above.

At block 1116, a circular circuit board is optionally electrically coupled to the plurality of circuit boards. The circular circuit board may include at least one side with electrical components. For example, the circular circuit board may include one or more IC chips. The circular circuit board may be disposed parallel to the common plane of the plurality of circuit boards. Additionally or alternatively, the circular circuit board may be disposed within the opening of the ferrimagnetic cup opposite the planar base. The circular circuit board may be coupled to the plurality of circuit boards via a connector, such as connector 420 as described above. The connector may be configured to distribute power from the plurality of circuit boards to the electrical components of circular circuit board. The connector may also be configured to transmit data between the circular circuit board and one or more of the plurality of circuit boards. Additionally or alternatively, the connector may couple the circular circuit board to the radio antenna via an antenna connector, such as antenna connector 135 as described above.

At block 1118, a metallic shield is optionally connected to the circular circuit board. The metallic shield may be made from one or more metallic compounds and be configured to reduce the effects of external EMI on the electrical components of the circular circuit board. The metallic shield may be continuously connected around a circumference of the circular circuit board. The continuous connection between the metallic shield and the circular circuit board may act as a humidity barrier, thereby reducing the potential for unwanted accumulation of humidity in and around the electrical components of the circular circuit board.

It should be appreciated that a brain implant or other system and a respective control system for the brain implant can have one or more microprocessors/processing devices that can further be a component of the overall apparatuses. The control systems are generally proximate to their respective devices, in electronic communication (wired or wireless) and can also include a display interface and/or operational controls configured to be handled by a user to monitor the respective systems, to change configurations of the respective systems, and to operate, directly guide, or set programmed instructions for the respective systems, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

In some embodiments, the apparatuses and methods of the present disclosure can be used in connection with neurosurgical techniques. However, one skilled in the art would recognize that neurosurgical techniques are a non-limiting application, and the systems and methods of the present disclosure can be used in connection with any biological tissue. Biological tissue can include, but is not limited to, the brain, muscle, liver, pancreas, spleen, kidney, bladder, intestine, heart, stomach, skin, colon, and the like.

The systems and methods of the present disclosure can be used on any suitable multicellular organism including, but not limited to, invertebrates, vertebrates, fish, bird, mammals, rodents (e.g., mice, rats), ungulates, cows, sheep, pigs, horses, non-human primates, and humans. Moreover, biological tissue can be ex vivo (e.g., tissue explant), or in vivo (e.g., the method is a surgical procedure performed on a patient).

The teachings of the invention provided herein can be applied to other systems and apparatuses, not necessarily the system or apparatus described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. A space-saving, wrapped cylindrical electronic apparatus comprising:
    a plurality of at least four circuit boards arranged to form sides of a five-or-greater sided geometric prism that are perpendicular to a common plane, wherein each circuit board of the plurality of circuit boards includes a side with electrical components;
    the plurality of circuit boards comprises at least half of the five-or-greater sided geometric prism such that the circuit boards wrap at least halfway around said geometric prism;
    a connector on one of the circuit boards configured to receive power; and
    flex cables connecting adjacent circuit boards in series, the flex cables distributing power received from the connector to each of the circuit boards in series.

2. The apparatus of claim 1, further comprising:
    a power coil disposed around the geometric prism and electrically coupled to the plurality of circuit boards, the power coil comprising a planar conducting material having a length, wherein the length of the planar conducting material is wrapped in a spiral thereby forming a geometric cylinder.

3. The apparatus of claim 1, further comprising:
    a cylindrical button battery around which the circuit boards are arranged.

4. The apparatus of claim 1, further comprising:
    a radio antenna electrically coupled to at least one of the plurality of circuit boards, the radio antenna forming a circular loop with a circumference in a first plane, the first plane being parallel to the common plane.

5. The apparatus of claim 1, further comprising:
a chassis, wherein each circuit board of the plurality of circuit boards is mechanically secured to the chassis.

6. The apparatus of claim 1, further comprising:
a ferrimagnetic cup having a cylindrical side wall; and
wherein the plurality of circuit boards are arranged within an interior of the ferrimagnetic cup such that the side with electrical components of each circuit board of the plurality of circuit boards faces the cylindrical side wall.

7. The apparatus of claim 6, wherein the ferrimagnetic cup is configured to align the plurality of circuit boards in a predefined orientation within the ferrimagnetic cup.

8. The apparatus of claim 1, further comprising:
a circular circuit board electrically coupled to the plurality of circuit boards, the circular circuit board disposed parallel to the common plane.

9. The apparatus of claim 8, further comprising:
a metallic shield connected to the circular circuit board, wherein the metallic shield is continuously connected around a circumference of the circular circuit board.

10. A three dimensional wrapped cylindrical electronic apparatus comprising:
a power coil comprising a planar conducting material having a length, wherein the length of the planar conducting material is wrapped in a spiral thereby forming a geometric cylinder;
a circuit board, including a side with electrical components, electrically coupled to the power coil and disposed within an interior of the geometric cylinder such that the side of the circuit board faces the planar conducting material; and
a ferrimagnetic cup having a planar base and a cylindrical side wall, wherein the ferrimagnetic cup is disposed within the geometric cylinder such that the cylindrical side wall separates the power coil from the circuit board.

11. The apparatus of claim 10, further comprising:
a radio antenna electrically coupled to the circuit board, the radio antenna forming a circular loop, wherein the radio antenna is arranged on an exterior surface of the ferrimagnetic cup such that the circular loop is parallel to the planar base of the ferrimagnetic cup.

12. The apparatus of claim 10, further comprising:
a chassis arranged within the ferrimagnetic cup, wherein the circuit board is secured to the chassis.

13. The apparatus of claim 10, further comprising:
a circular circuit board electrically coupled to the circuit board, the circular circuit board disposed parallel to the planar base of the ferrimagnetic cup and perpendicular to the side of the circuit board.

14. A method of manufacturing a space-saving, wrapped cylindrical electronic apparatus, the method comprising:
providing a plurality of at least four circuit boards, each circuit board of the plurality of circuit boards including a side with electrical components, wherein at least one circuit board of the plurality of circuit boards includes a connector configured to receive power;
arranging the plurality of circuit boards to form sides of a five-or-greater sided geometric prism that are perpendicular to a common plane, wherein the plurality of circuit boards comprises at least half of the five-or-greater sided geometric prism such that the plurality of circuit boards wraps at least halfway around said geometric prism; and
connecting adjacent circuit boards in series using flex cables, the flex cables distributing power received from the connector to each circuit board of the plurality of circuit boards in series.

15. The method of claim 14, further comprising:
electrically coupling a power coil to the plurality of circuit boards, the power coil comprising a planar conducting material having a length; and
wrapping the length of the planar conducting material around the geometric prism thereby forming a geometric cylinder.

16. The method of claim 14, further comprising:
providing a ferrimagnetic cup having a cylindrical side wall; and
arranging the plurality of circuit boards within an interior of the ferrimagnetic cup such that the side with electrical components of each circuit board of the plurality of circuit boards faces the cylindrical side wall.

17. The method of claim 14, further comprising:
electrically coupling a radio antenna to at least one of the plurality of circuit boards, the radio antenna forming a circular loop with a circumference in a first plane; and
arranging the circular loop adjacent to the plurality of circuit boards such that the first plane is parallel to the common plane.

18. The method of claim 14, further comprising:
mechanically securing each circuit board of the plurality of circuit boards to a chassis.

19. The method of claim 14, further comprising:
electrically coupling a circular circuit board to the plurality of circuit boards; and
disposing the circular circuit board parallel to the common plane.

20. The method of claim 19, further comprising:
connecting a metallic shield to the circular circuit board, wherein the metallic shield is continuously connected around a circumference of the circular circuit board.

* * * * *